(12) United States Patent
Kojima

(10) Patent No.: US 8,597,220 B2
(45) Date of Patent: Dec. 3, 2013

(54) PINCER NAIL CORRECTION TOOL

(75) Inventor: Yoshiko Kojima, Osaka (JP)

(73) Assignee: Bigbang Co., Ltd., Osaka (JP)

( * ) Notice: Subject to any disclaimer, the term of this patent is extended or adjusted under 35 U.S.C. 154(b) by 484 days.

(21) Appl. No.: 12/744,453

(22) Filed: May 24, 2010

(65) Prior Publication Data

US 2010/0268143 A1 Oct. 21, 2010

Related U.S. Application Data

(63) Continuation of application No. PCT/JP2008/071769, filed on Dec. 1, 2008.

(30) Foreign Application Priority Data

Dec. 5, 2007 (JP) ................................. 2007-314622

(51) Int. Cl.
*A61F 5/00* (2006.01)
(52) U.S. Cl.
USPC ............................................. 602/31; 128/893
(58) Field of Classification Search
USPC ............................................. 602/31; 128/893
See application file for complete search history.

(56) References Cited

U.S. PATENT DOCUMENTS 2,920,621 A * 1/1960 Fettig .............................. 602/31
5,370,140 A * 12/1994 Meyerovich ................... 132/200

FOREIGN PATENT DOCUMENTS

| JP | 2006-314748 A | 11/2006 |
| JP | 2007-185203 A | 7/2007 |

* cited by examiner

*Primary Examiner* — Patricia Bianco
*Assistant Examiner* — Camtu Nguyen
(74) *Attorney, Agent, or Firm* — Birch, Stewart, Kolasch & Birch, LLP

(57) ABSTRACT

A pincer nail correction tool for remedying a pincer nail of a toe as the nail grows by bonding a necessary part separated from the body to the pincer nail. The tool includes a flat operating portion gripped before the necessary part is bonded and rotated in the direction in which the pincer nail is remedied, a thin-sheet abutting portion extending from the flat surface on one side of the operating portion and projecting straight toward the distal end, a thin-sheet engaging portion narrower than the abutting portion in the surface direction and extending from the surface on the other side of the operating portion substantially parallel with the abutting portion, and a bottom extending from one end face of the operating portion toward the distal end and connecting the abutting portion with the engaging portion to form a J-shaped cross-section. The projection length of the abutting portion is longer than that of the engaging portion.

10 Claims, 13 Drawing Sheets

EQ3

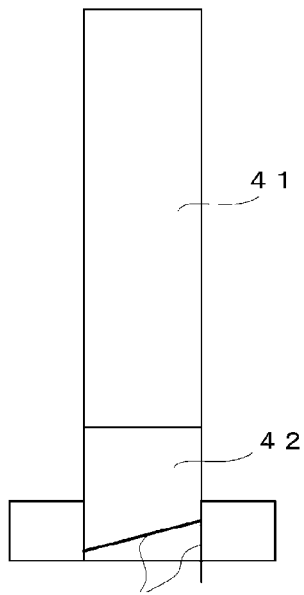
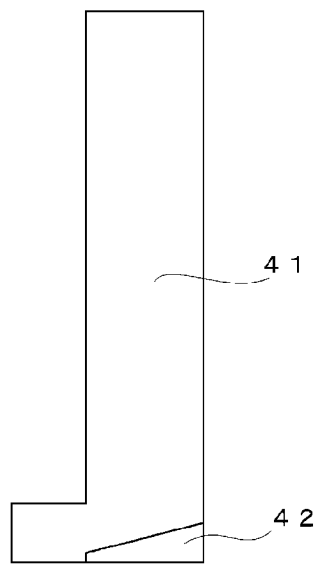
FIG.10A        FIG.10B
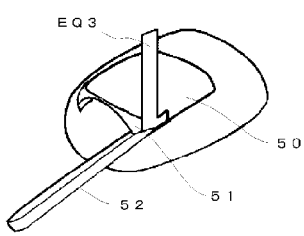
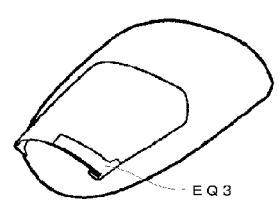
FIG.11A        FIG.11B
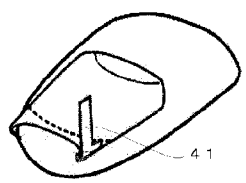
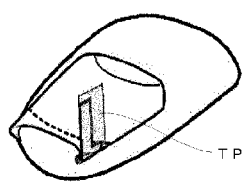
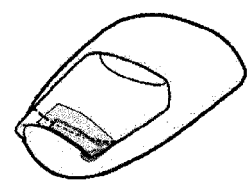
FIG.11C        FIG.11D        FIG.11E

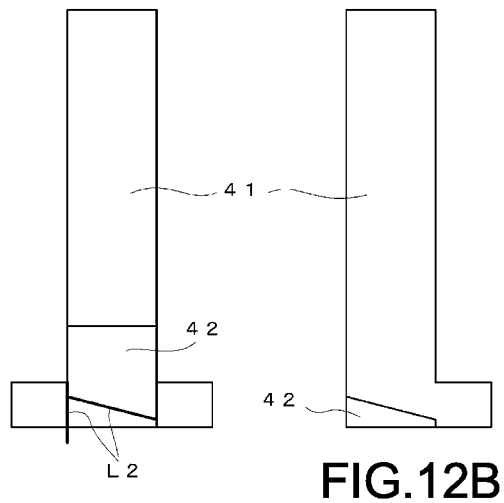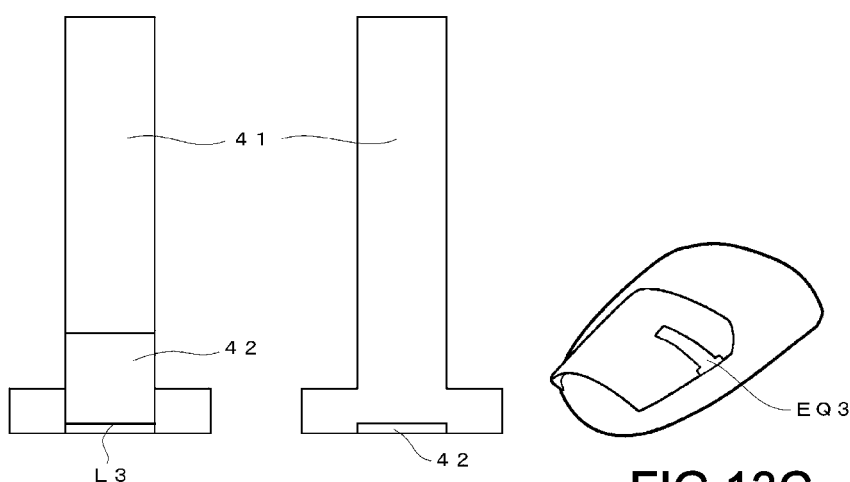

PINCER NAIL CORRECTION TOOL

TECHNICAL FIELD

The present invention relates to a pincer nail correction tool for naturally remedying a pincer nail as the nail grows.

BACKGROUND ART

As a result of continuous wearing of shoes having narrowed shoes toes such as high-heeled shoes, a nail of a toe can be extremely curved and deformed into a pincer nail. As a tool for correcting such a pincer nail, the present applicant proposed a correction tool of Patent Document 1.

This correction tool is inserted on either side of a distal end of a nail, and is moved in the direction in which the curve of the nail is to be corrected. By securing the correction tool in this state, the pincer nail is corrected as the nail grows. This tool wins great popularity.

[Patent Document 1] Japanese Patent Publication No. 3393865

DISCLOSURE OF THE INVENTION

Problems to be Solved by the Invention

However, the above-mentioned correction tool is interfered by the skin of a toe and cannot be inserted deeply in a nail because of its structure. Therefore, it is impossible to sufficiently ensure a bonding face with the nail, and stress by the growing nail will concentrate on a narrow bonding site, so that the possibility of cracking of the nail cannot be denied.

Also, since it is somewhat difficult to correct pincer nails of various degrees of curvature with a single correction tool, development of a correction tool accepting various degrees of curvature of pincer nails is highly demanded. Furthermore, development of a tool capable of appropriately accepting a nail tip that is infected by ringworm fungi is also demanded.

The present invention was devised in consideration of the above problems, and it is an object of the invention to provide a correction tool capable of widely dispersing pressure during correction of a pincer nail, and avoiding cracking and the like of the nail. It is another object of the invention to provide a correction tool exerting optimum correcting power in accordance with the degree of curvature of the nail and the like.

Means for Solving the Problems

In order to achieve the objects described above, the invention provides a pincer nail correction tool for remedying a pincer nail of a toe as the nail grows by integrally bonding a necessary part of the correction tool separated from a an operating flat plate of the correction tool to the pincer nail, the tool including: a flat operating portion gripped before the necessary part is bonded and to be rotated in a direction in which the pincer nail is remedied; a thin-sheet abutting portion extending from a flat surface on one side of the operating portion and projecting straight toward a distal end; a thin-sheet engaging portion narrower than the abutting portion in a surface direction and extending from a flat surface on another side of the operating portion substantially parallel with the abutting portion; and a bottom portion extending from one end face of the operating portion toward the distal end and connecting the abutting portion with the engaging portion to form a J-shaped cross-section, wherein a projection length of the abutting portion is longer than that of the engaging portion. The necessary part of the correction tool, which is bonded to the pincer nail and is separated from the operating flat plate, is formed of the abutting portion, the engaging portion, and the bottom portion.

The pincer nail includes those referred to as an ingrown nail (the condition that a corner of a nail sticks into a soft tissue (flesh) like a splinter to cause inflammation), a trumpet nail (the condition that a nail is heavily caught into the skin from both sides), a splinter nail (the condition that a part of a nail having a splinter-like shape sticks into the skin), and a spirally wound nail.

In order to prevent the superficial face of the nail from being cracked by ensuring a sufficient adhesion area to the superficial face of the nail and widely dispersing pressure during correction of the pincer nail, the abutting portion is preferably formed into a substantially rectangular shape.

Preferably, the engaging portion has a connecting part continuing from the operating portion, and an engaging body part narrower than the connecting part in the surface direction. Usually, in accordance with a yellow line of the nail formed into an arc shape (the borderline where a nail bed and a nail plate separate from each other), the narrow engaging body part can be inserted up to a limit position, and a sufficient adhesion area to the back face of the nail can be ensured.

Preferably, the engaging body part is formed to be gradually narrower toward the distal end. In an early stage of correction, since the adhesion area to the back face of the nail is large, strong correcting power is exerted particularly at a nail tip end. Thereafter, the curved state is corrected as the nail grows, so that there arises no problem even if the adhesion area reduces.

Preferably, the connecting part and the engaging body part are connected with each other via an intermediate part that is formed to be gradually narrower toward the distal end. By providing the intermediate part, the engaging body part can be formed to have a constant width. Therefore, a wide adhesion area to the back face of the nail can be ensured for a long time, and strong correcting power is exerted.

The abutting portion may have a proximal end abutting part continuing from the operating portion, and a distal end abutting part narrower than the proximal end in the surface direction. Provision of the narrow distal end abutting part ensures a sufficient insertion depth. Therefore, a sufficient adhesion area to the superficial face of the nail can be ensured in a severe pincer nail.

In the above case, in the bottom portion, the distal end side of the engaging portion is preferably notched. A tip end of the engaging body part can be inserted up to the limit position, and a sufficient adhesion area to the back face of the nail can be ensured.

Preferably, a plurality of holes are formed in the abutting portion. This facilitates the process of fixing the correction tool to the nail and scraping off a part of the correction tool excessively projecting from the nail.

The invention provides a pincer nail correction tool for remedying a pincer nail of a toe as the nail grows by integrally bonding a necessary part separated from an main body to the pincer nail, the tool including: an abutting portion formed to have a J-shaped cross section by folding a thin-sheet material and extending long toward a distal end; an engaging portion extending shorter than the abutting portion substantially parallel therewith; and a return portion connecting the abutting portion and the engaging portion. The necessary part, which is bonded to the pincer nail and is separated from the operating thick disc, is formed abutting portion, the engaging portion, and the return portion. Prior to use, an unnecessary part of the correction tool, namely the operating thick disc, is removed in accordance with a correction position of the nail.

This correction tool enables correction of a thin nail, as well as a nail in a toe other than a thumb which is conventionally considered to be difficult to correct, as well as in fingers.

In order to prevent the superficial face of the nail from being cracked by ensuring a sufficient adhesion area to the superficial face of the nail and widely dispersing the pressure during correction of the pincer nail, it is preferred that the proximal end side of the abutting portion is formed to be wide in the surface direction and formed to have a substantially T-shape in planar view as a whole.

The engaging portion may be formed in such a manner that the distal end side is notched into a trapezoidal shape. This greatly reduces the steps of processing the correction tool, and allows simplified attachment in a short period of time.

On the distal end side of the abutting portion, a thick operating portion may be provided continuously. This facilitates gripping of the correction tool.

The invention provides a pincer nail correction tool for remedying an ingrown nail of a toe as the nail grows by integrally bonding a necessary part separated from a main body to the ingrown nail, the tool including: a flat operating portion; a thin-sheet connecting portion extending from a flat surface on one side of the operating portion; a plate-like abutting portion extending from a flat face on another side of the connecting portion; and a hook-like engaging portion formed by folding a flat face on another side of the abutting portion, wherein the abutting portion is formed to be thicker than the connecting portion.

This correction tool may be used by being bonded on a surface of another correction tool after attaching the other correction tool on a pincer nail. In this case, besides a lateral end of the nail breaking into the skin, a tip end of the nail can be corrected at once.

Effects of the Invention

According to the present invention described above, by dispersing the pressure widely during correction of the pincer nail, it is possible to achieve safe correction while avoiding a fear of cracking of the nail, and further to draw up the lateral end of the nail over a wide range. In the present invention, even when a nail is infected by ringworm fungi, the nail can be corrected in the part excluding the infected part, and even a severe ingrown nail can be corrected.

BRIEF DESCRIPTION OF THE DRAWINGS

FIGS. 10A-10B include views each showing a method of using the correction tool EQ3.

FIGS. 11A-11E include another views each showing a method of using the correction tool EQ3.

FIGS. 12A-12C include views each showing another method of using the correction tool EQ3.

FIGS. 13A-13C include views each showing further another method of using the correction tool EQ3.

FIGS. 14A-14B include views respectively showing a correction tool EQ3' and a correction tool EQ3" as further examples of the correction tool EQ3.

BEST MODES FOR CARRYING OUT THE INVENTION

The present invention will be described below based on embodiments. FIGS. 1A-1E include views each showing a pincer nail correction tool EQ1 according to a first embodiment of the present invention, namely a front view FIG. 1A a plan view FIG. 1B, a bottom view FIG. 1C, a perspective view FIG. 1D, and an A-A cross section view FIG. 1E.

The correction tool EQ1 includes a flat operating portion 1 gripped during use, a thin-sheet abutting portion 2 extending from a back side of a left lateral face of the operating portion 1 and projecting straight toward a distal end, a thin-sheet engaging portion 3 narrower than the abutting portion 2 and extending from a front side of the left lateral face of the operating portion 1 substantially parallel with the abutting portion 2, and a bottom portion 4 extending from a bottom side of the left lateral face of the operating portion 1 toward the distal end and connecting the abutting portion 2 and the engaging portion 3 to form a substantially J-shaped cross section, which are integrally formed of transparent plastic (ABS resin). The correction tool EQ1 has a lateral length of, for example, about 52 mm.

Figure 1A:
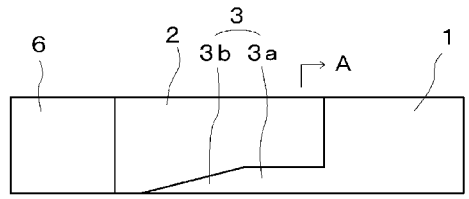
FIGS. 1A-1E include views each showing a correction tool EQ1 according to a first embodiment of the present invention.
Figure 1B:
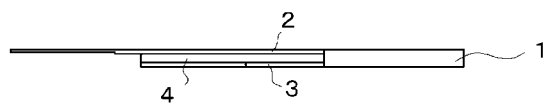
Figure 1C:
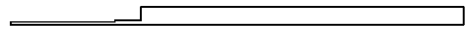
Figure 1D:
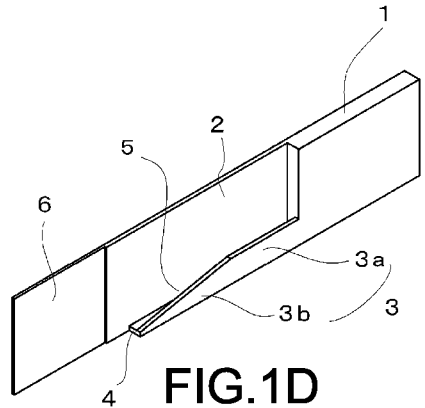
Figure 1E:
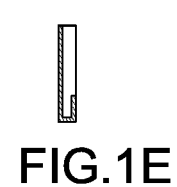

As shown in FIG. 1D, an insertion groove 5 having a substantially J-shaped cross section is formed by the abutting portion 2, the engaging portion 3 and the bottom portion 4. A projection length of the abutting portion 2 is larger than those of the engaging portion 3 and the bottom portion 4.

The abutting portion 2 formed into a substantially rectangular shape has the same width in the surface direction (vertical direction) as that of the operating portion 1. The abutting portion 2 is provided with a thin-thickness portion 6 extending toward the distal end from rather a center of the distal end side (left side). The thin-thickness portion 6 is a rough mark in cutting the correction tool EQ1 as will be described later, and is formed to be thinner than the abutting portion 2 for ease of cutting.

The engaging portion 3 is made up of a connecting part 3a having a width in the vertical direction narrower than that of the operating portion 1 and continuing from the operating portion 1, and an engaging body part 3b extending from the connecting part 3a to be further narrower in the vertical direction. The engaging body part 3b is diagonal so that it is gradually narrowed toward the bottom portion 4.

Figure 2:
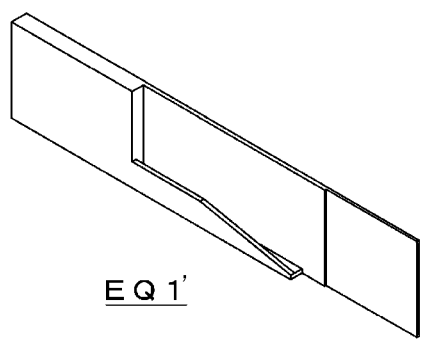
FIG. 2 is a view showing a correction tool EQ1' as another example of the correction tool EQ1.
Figure 3A:
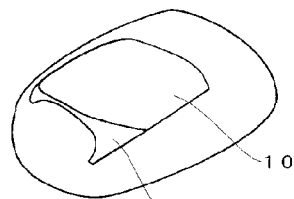
FIGS. 3A-3I include views each showing a method of using the correction tool EQ1.

Since the correction tool EQ1 of the first embodiment is configured as described above, it will be used for a case where a part to be corrected in a pincer nail of a toe shown in FIG. 3A is situated on the observer's right of the subject. Therefore, when a part to be corrected is situated on the observer's left of the subject, a correction tool EQ1' having a configuration shown in FIG. 2 will be used.

Next, a method of using the correction tool EQ1 according to the first embodiment will be described with reference to FIGS. 3A to 4E. Prior to use of the correction tool EQ1, a foot of a subject is wiped with a steaming towel or the like. The foot may be dipped in a foot bath (foot bath machine). In this case, the foot should be just rinsed so that water will not enter the nail overly.

Figure 3B:
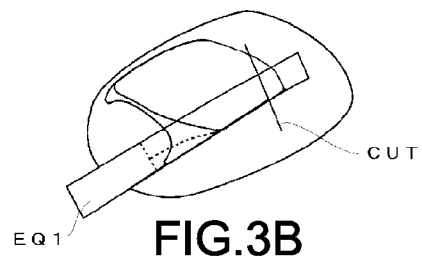

Next, as shown in FIG. 3B, a tip end of the engaging portion 3 is brought into abutment with the vicinity of a proximal end of a nail tip 11 (free edge) of the pincer nail 10 of the subject. Then a part of the thin-thickness portion 6 of the abutting portion 2 projecting from the nail 10 is cut. Next, a gel 13 is applied to the vicinity of the lower side of an inner face of the abutting portion 2 of the correction tool EQ1. Then, a blush (not shown) is immersed with an activator 14 (activating agent), and the gel 13 placed on the abutting portion 2 is mixed with the activator 14 by using the blush, and the gel 13 is rubbed with the blush so that it spreads into the insertion groove 5 defined by the abutting portion 2, the engaging portion 3 and the bottom portion 4. At this time, an upper part of the inner face of the abutting portion 2 is kept from being rubbed with the gel. Here, the gel 13 is mainly based on ethyl-2-cyanoacrylate, polymethyl methacrylate, and hydroquinone. The activator 14 is mainly based on ethyl acetate and dimethyl-P-toluidine, and promotes drying of the gel 13.

Figure 3C:
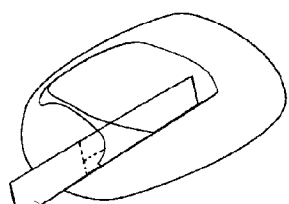
Figure 3D:
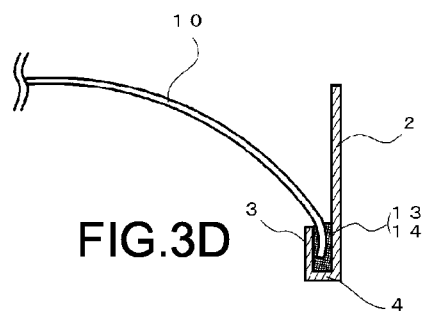

Next, as shown in FIGS. 3C-3D, a lateral nail fold of the subject is opened so that the lateral end of the nail 10 is visible, and the insertion groove 5 is inserted into a proximal end of the nail tip 11. Then the lower side of the outer face of the abutting portion 2 is pushed to such an extent that the engaging portion 3 adheres with the back side of the nail tip 11 and the lower side of the abutting portion 2 adheres with the superficial face of the nail 10 and the nail tip 11 via the gel 13.

Figure 3E:
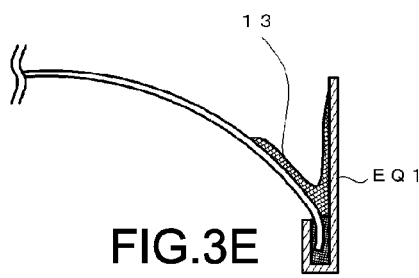
Figure 3F:
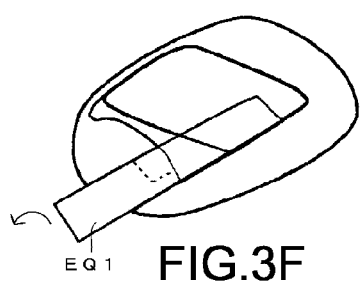

After the gel 13 cures and the right lateral end of the nail 10 and the lower side of the correction tool EQ1 are fixed, the gel 13 is further poured between the superficial face of the nail 10 and the abutting portion 2 as shown in FIG. 3E. Next, as shown in FIG. 3F, the operating portion 1 is rotated to bring down the correction tool EQ1, to thereby join the superficial face of the nail 10 and the upper side of the abutting portion 2. Then, the correction tool EQ1 is kept while it is brought down until the gel 13 cures, so that the correction tool EQ1 and the nail 10 of the subject are integrated with each other while the curved state of the pincer nail is corrected.

Figure 3G:
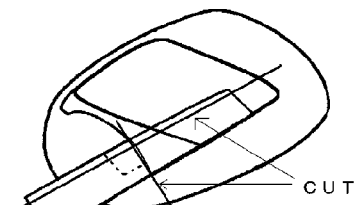
Figure 3H:
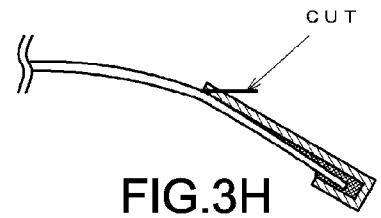
Figure 3I:
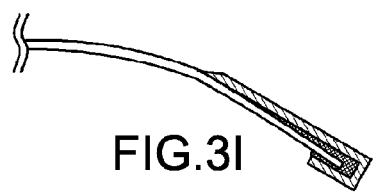

Next, as shown in FIG. 3G, unnecessary parts excessively projecting from the nail 10 at the operating portion 1, the abutting portion 2 and the engaging portion 3 of the correction tool EQ1 are scraped off, leaving only a necessary part adhering to the nail. Also as shown in FIG. 3H, an upper end of the abutting portion 2 is scraped off to level the superficial face of the nail 10 and the abutting portion 2. The nail 10 and the correction tool EQ1 are then scraped and shaped to provide a good appearance as a whole (see FIG. 3I).

Figure 4A:
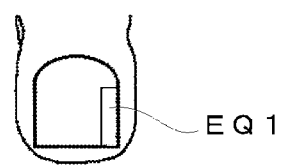
FIGS. 4A-4E include another views each showing a method of using the correction tool EQ1.
Figure 4B:
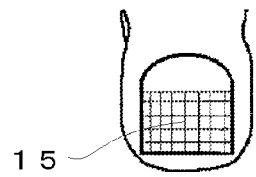
Figure 4C:
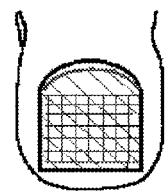

As a result of these treatments, the nail 10 is integrated with the correction tool EQ1 and is finished into the state as shown in FIG. 4A. Next, for improving the durability of the correction tool EQ1, a fiber glass 15 is bonded onto the nail 10. First, the rectangular fiber glass 15 is bonded onto the superficial face of the nail 10, and a part running over the superficial face of the nail 10 is cut (see FIG. 4B). Then a resin is applied onto the fiber glass 15 bonded on the superficial face of the nail 10, so that the fiber glass 15 adheres securely onto the superficial face of the nail 10 (FIG. 4C). As a result, fibrous mesh of the fiber glass 15 is almost invisible. The resin is mainly based on ethyl-2-cyanocrylate and hydroquinone.

Figure 4D:
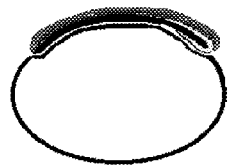
Figure 4E:
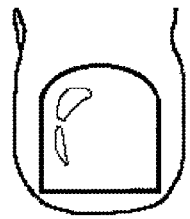

Lastly, the gel 13 and the activator 14 are spread over the entire superficial face of the nail 10 onto which the fiber glass 15 is bonded, and the entire superficial face of the nail 10 is secured with the gel. As a result, the nail 10 is secured in a corrected condition, and the correcting treatment of the pincer nail completes. FIG. 4D and FIG. 4E are a front view and a plan view of a nail in a complete state, respectively.

In the correction tool EQ1 of the first embodiment, since the projection length of the abutting portion 2 is longer than that of the engaging portion 3, the correction tool EQ1 is secured over a large range on the superficial face of the nail. As a result, safety correction is realized by widely dispersing pressure during correction of the pincer nail and avoiding the fear of cracking of the nail. Also, by forming the abutting portion 2 into a substantially rectangular shape, it is possible to ensure a sufficient adhesion area to the superficial face of the nail.

Since the correction tool EQ1 is made of transparent plastic, it can be easily cut or deformed. Therefore, after securing the correction tool EQ1 on the nail of the subject, the shape of the nail of the subject can be seen through the correction tool EQ1. As a result, the correction tool EQ1 may be cut in accordance with the shape of the nail. Further, since the fiber glass 15 that turns into transparent together with the transparent correction tool EQ1 is bonded on the superficial face of the nail, the subject has no uncomfortable feeling during correction of the nail by attachment of the correction tool EQ1. Also good-looking correction can be achieved so that attachment of the correction tool EQ1 is almost unrecognized.

Figure 5A:
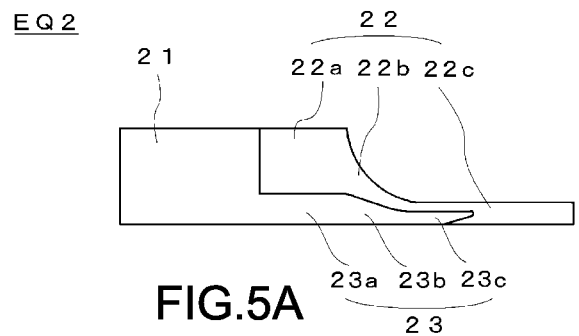
FIGS. 5A-5C include views each showing a correction tool EQ2 according to a second embodiment of the present invention.
Figure 5B:
Figure 5C:
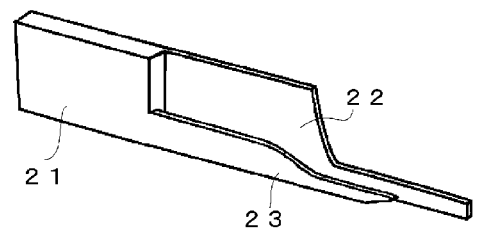

Next, FIGS. 5A-5C include views each showing a pincer nail correction tool EQ2 of a second embodiment of the present invention, namely a front view FIG. 5A, a plan view FIG. 5B, and a perspective view FIG. 5C.

Figure 7A:
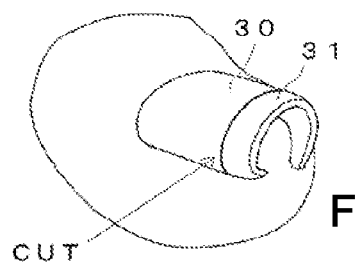
FIGS. 7A-7E include views each showing a method of using the correction tool EQ2.

The correction tool EQ2 is used with a severe pincer nail which has little gap between the skin and the nail as shown in FIG. 7A, so that the bottom portion 4 of the correction tool EQ1 of the first embodiment cannot enter between the skin and the nail. It is also preferably used with a spiral nail in which the nail is wound several times. The correction tool EQ2 includes a flat operating portion 21 gripped during use, a thin-sheet abutting portion 22 extending from a back side of a right lateral face of the operating portion 21 and projecting toward a distal end (rightward), a thin-sheet engaging portion 23 narrower than the abutting portion 22 in the vertical direction and extending from a front side of the right lateral face of the operating portion 21 substantially parallel with the abutting portion 22, and a bottom portion 24 extending from a bottom side of the right lateral face of the operating portion 21 and connecting the abutting portion 22 and the engaging portion 23 to form a J-shaped cross section. The correction tool EQ2 has a lateral length of, for example, about 56 mm.

As shown in FIG. 5C, a projection length of the abutting portion 22 is longer than those of the engaging portion 23 and the bottom portion 24. The abutting portion 22 is made up of a proximal end abutting part 22a continuing from the operating portion 21 and having the same width in the surface direction (vertical direction) with the operating portion 21, a distal end abutting part 22c formed into a narrowed rectangular shape, and an intermediate part 22b connecting the proximal end abutting part 22a and the distal end abutting part 22c and having a gradually narrowed width.

The engaging portion 23 is made up of a connecting part 23a having a narrower width in the vertical direction than the operating portion 21 and continuing from the operating portion 21, an engaging body part 23c having a narrower width in the vertical direction than the connecting part 23a, and an intermediate part 23b connecting the connecting part 23a and the engaging body part 23c and having a gradually narrowed width.

The bottom portion 24 has a projection length shorter than that of the engaging portion 23. The bottom portion 24 is formed in the shape of a notch with respect to the abutting part 22 and the engaging portion 23. In other words, the abutting portion 22 and the engaging portion 23 are formed in the shape of a fork projecting from the bottom portion 24.

Figure 6:
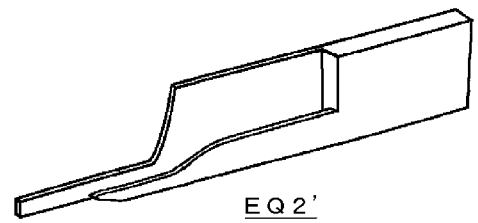
FIG. 6 is a view showing a correction tool EQ2' as another example of the correction tool EQ2.

Since the correction tool EQ2 of the second embodiment is formed as described above, it is used in a case where the part to be corrected in the pincer nail of the toe shown in FIG. 7A is situated on the observer's left of the subject. Therefore, when the part to be corrected is situated on the observer's right of the subject, a correction tool EQ2' having a configuration as shown in FIG. 6 is used.

Next, with reference to FIGS. 7A-7E, a method of using the correction tool EQ2 configured as described above will be described. First, a sanitary treatment is conducted similarly to the first embodiment. Then as shown in FIG. 7A, a tip end of a nail tip 31 of a nail 30 is cut into a predetermined length. Then, similarly to the first embodiment, the gel and the activator are mixed together and applied onto the lower side of the inner face of the abutting portion 22, the engaging portion 23 and the bottom portion 24. At this time, the upper side of the inner face of the proximal end abutting part 22a and the intermediate part 22b of the abutting portion 22 is kept from being rubbed with the gel.

Figure 7B:
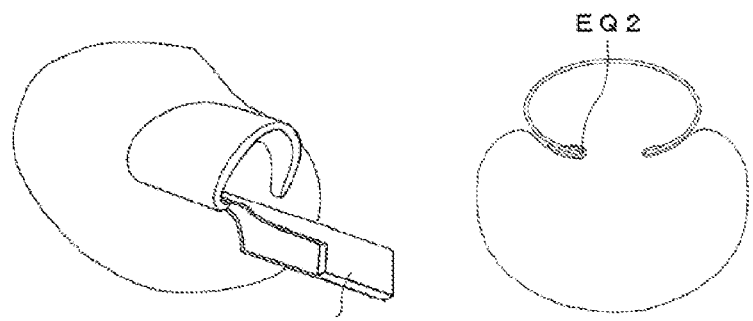

As shown in FIG. 7B, the correction tool EQ2 is inserted in a lateral end of the nail tip 31 to such an extent that the abutting portion 22 engages with the superficial face of the nail 30 and the engaging body part 23c engages with the back face of the nail 30 while the bottom portion 24 does not come into abutment with the skin of the toe.

Figure 7C:
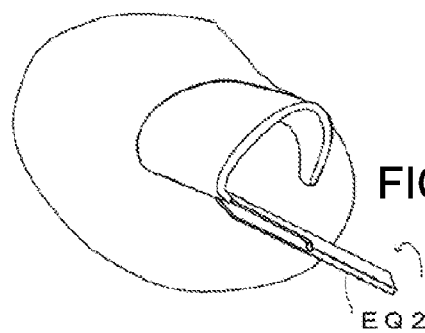

After a while, the gel cures, and the lateral end of the nail 30 and the lower side of the correction tool EQ2 are secured. After the securing, similarly to the first embodiment, the gel is further poured between the superficial face of the nail projecting from the toe and the upper sides of the inner faces of the proximal end abutting part 22a and the intermediate part 22b. Then, as shown in FIG. 7C, the operating portion 21 is twisted to join the superficial face of the nail and the upper lateral face of the abutting portion 22. The gel cures while the correction tool EQ2 is kept twisted, and the correction tool EQ2 and the nail 30 of the subject are integrated with each other while the curved state of the pincer nail is corrected.

In the following, similarly to the first embodiment, a part excessively projecting from the nail 30 of the correction tool EQ2 is scraped off. A fiber glass is then bonded onto the superficial face of the nail 30, and the gel is applied thereon, so that the nail 30 is secured in a corrected state.

In the correction tool EQ2 of the second embodiment, since the projection length of the abutting portion 22 is longer than that of the engaging portion 23, the correction tool EQ2 is fixed over a large range of the superficial face of the nail. As a result, it is possible to widely disperse pressure during the correction of the pincer nail, thereby realizing safe correction by avoiding the fear of cracking of the nail.

Further, even in the case of a severe pincer nail where there is no gap between the skin and the nail and the bottom portion 4 cannot enter between the skin and the nail with the correction tool EQ1 of the first embodiment, the correction tool EQ2 can be fixed to the nail as if the nail were gripped with tweezers without causing abutment of the skin of the toe with the bottom portion 24 because the engaging portion 23 is formed into a fork projecting from the bottom portion 24 together with the abutting portion 22.

Figure 7D:
Figure 7E:
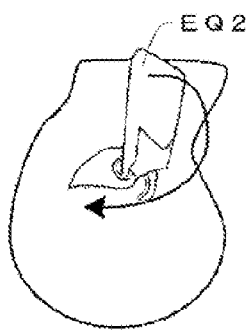

Further, the correction tool EQ2 can be used to a spiral nail in which the nail is wound several times, for example, as shown in FIG. 7D. As shown in FIG. 7E, the correction tool EQ2 is inserted into a tip end of the spiral nail. Then, the operating portion 21 is rotated and secured to allow correction of the nail in the condition where the spiral is remedied.

Figure 8A:
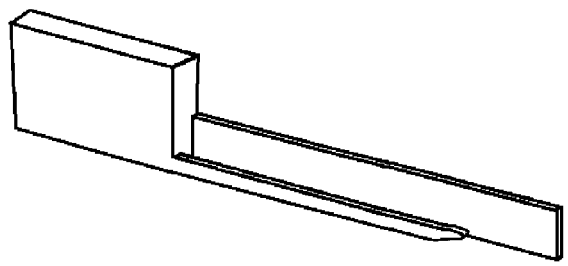
FIGS. 8A-8B include views respectively showing a correction tool EQ2" and a correction tool EQ2'" as further examples of the correction tool EQ2.

In the case of the present embodiment, the correction tool EQ2 may be formed as a correction tool EQ2" according to a modified example shown in FIG. 8A. In the correction tool EQ2", the abutting portion is extended from a substantial center in the vertical direction of the operating portion, the engaging portion is formed to extend straight from the proximal end to the distal end, and the abutting portion and the engaging portion are formed to project from the bottom in the shape of a fork.

Figure 8B:
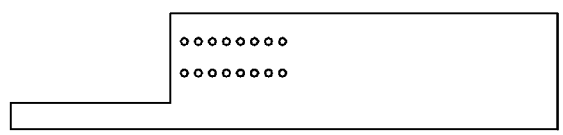

There may be a correction tool EQ2''' as a modified example shown in FIG. 8B. The abutting portion of the correction tool EQ2''' is made up of a proximal end abutting part 22a continuing from the operating portion 21 and having the same width in the surface direction (vertical direction) as the operating portion 21, and a distal end abutting part 22b extending from the distal end direction (right direction) of the distal end abutting part 22a and formed into a rectangular shape narrow in the surface direction. As shown in FIG. 8B, on the surface of the proximal end abutting part 22a, a plurality of holes 22h . . . 22h are formed in two lines and 8 columns in the center of the vertical direction.

In this correction tool EQ2''', since the plurality of holes 22h are formed, excellent workability is provided in securing to a nail and scrapping off the part of the correction tool excessively projecting from the nail.

Figure 9C:
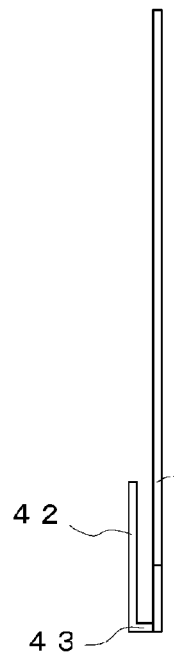
FIGS. 9A-9G include views each showing a correction tool EQ3 according to a third embodiment of the present invention.
Figure 9A:
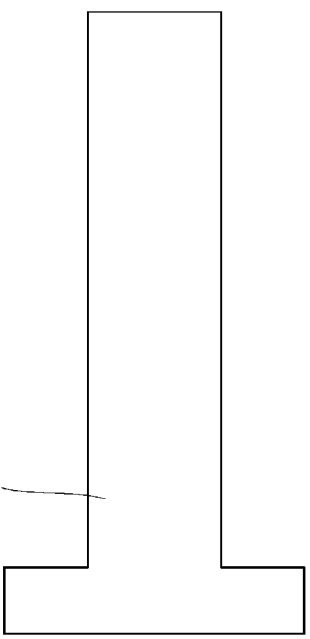
Figure 9B:
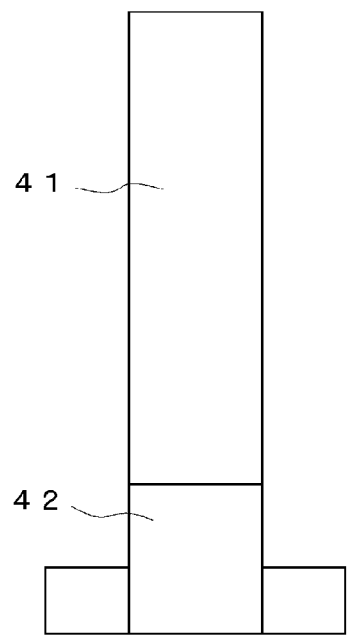
Figure 9D:
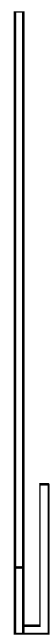
Figure 9E:
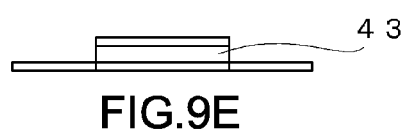
Figure 9F:
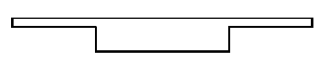
Figure 9G:
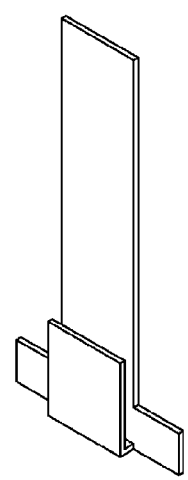

Next, FIGS. 9A-9G include views each showing a pincer nail correction tool EQ3 according to a third embodiment of the present invention, namely a front view FIG. 9A, a back view FIG. 9B, a left lateral view FIG. 9C, a right lateral view FIG. 9D, a plan view FIG. 9E, a bottom view FIG. 9F, and a perspective view FIG. 9G.

The correction tool EQ3 is used for correction of a mild pincer nail and an ingrown nail, and includes an abutting portion 41 extending long toward the distal end (upward direction), an engaging portion 42 shorter than the abutting portion 41 and extending upward substantially parallel with the abutting portion 41, and a return portion 43 connecting the abutting portion 41 and the engaging portion 42 on the proximal end side, thereby having a J-shaped cross section as a whole. The correction tool EQ3 is also formed of transparent plastic, and is preferably formed of plastic harder than ABS resin. The correction tool EQ3 has a vertical length of about 24 mm.

As shown in FIG. 9A, the proximal end side of the abutting portion 41 is formed to be wider in the surface direction (lateral direction), and the abutting portion 41 is formed into a T-shape in planar view as a whole.

Since the correction tool EQ3 of the third embodiment is configured as described above, either one of left and right pincer nails can be corrected by using the identical correction tool EQ3.

Next, with reference to FIGS. 10A, 10B, 11A, and 11B, a method of using the correction tool EQ3 configured as described above will be described. First, a sanitary treatment is conducted similarly to the first embodiment. Then, for correction of a right lateral end of a nail tip 51 of a nail 50, the abutting portion 41 and the engaging portion 42 of the correction tool EQ3 are cut along a cut line L1 as shown in the back view of the correction tool EQ3 in FIG. 10A (see FIG. 10B). Then the mixture of the gel and the activator is applied to the proximal end side of the abutting portion 41, the engaging portion 42 and the bottom portion 43. At this time, the upper side of the abutting portion 41 is kept from being rubbed with the gel.

As shown in FIG. 11A, the correction tool EQ3 is inserted into the right lateral end of the nail tip 51, and the proximal end side of the abutting portion 41 is fixed to the superficial face of the nail 50 as well as the engaging portion 42 is fixed to the back face of the nail 50. In this case, the correction tool EQ3 may be inserted into the nail tip 51 with use of tweezers 52.

After the gel cures to secure the lateral end of the nail 50 and the proximal end side of the correction tool EQ3, the gel is further poured between the superficial face of the nail 50 and the upper side of the abutting portion 41. Then, an upper side of the abutting portion 41 is bonded to the superficial face of the nail 50 while the nail tip 51 is gripped with the tweezers 52 and drawn outward (see FIG. 11B). After the gel cures, a part excessively projecting from the nail 50 in the correction tool EQ3 is cut. Further, by applying and fixing the gel on the peripheral edge of the abutting portion 41, the correction tool EQ3 and the nail 50 of the subject are integrated with each other while the curved state of the pincer nail is corrected.

When the left side end of the nail tip is corrected, the abutting portion 41 and the engaging portion 42 are cut according a cut line L2 shown in the back view of the correction tool EQ3 in FIG. 12A (see FIG. 12B). Then, the correction tool EQ3 is attached to the nail (see FIG. 12C).

When a lateral end of the nail other than the nail tip is corrected, only the engaging portion 42 is cut along a cut line L3 shown in the back view of correction tool EQ3 in FIG. 13A (see FIG. 13B). Then, the engaging portion 42 is inserted into the lateral end of the nail to conduct correction of the nail (see FIG. 13C).

In the correction tool EQ3 of the third embodiment, since the proximal end side of the abutting portion 41 is formed to be wide in the surface direction (lateral direction), pressure can be dispersed widely during correction of the pincer nail. As a result, a fear of cracking of the nail is avoided and safe correction can be realized. The lateral end of the nail can also be drawn up in a wide range.

While the proximal end side of the abutting portion 41 of the correction tool EQ3 is formed to have a substantially T-shape, the shape thereof may alternatively be a rectangular, trapezoidal, or rectangular. The shape of the abutting portion is not particularly limited as far as pressure applied during correction on the lateral end of the nail can be dispersed widely.

Further, by cutting the abutting portion 41 and the engaging portion 42 along the cut lines L1 and L2, the correction tool EQ3 may be used to either one of left and right nail tips. Also in a case where only the nail tip is wound, effective correction is realized. By cutting the engaging portion 42 along the cut line L3, it may be used to a lateral end of the nail other than the nail tip. Further, the correction tool EQ3 may be attached to a nail beside a part infected by ringworm fungi. Also after a severe pincer nail is corrected into a mild pincer nail by means of a correction tool EQ according to another embodiment, the correction tool EQ3 may be attached to a base of the nail to securely draw up only the base of the nail.

The correction tool EQ3 enables correction to a thin nail, as well as a nail in a toe other than a thumb which is conventionally considered to be difficult to correct and also in fingers. Further, in the correction tool EQ3, correction may be achieved without using the gel at the time of adhesion with the nail. In this case, the correction tool EQ3 is hooked on the nail tip, and a fabric tape TP larger than the abutting portion 41 is pasted on the surface of the abutting portion 41. The abutting portion 41 is brought down to the superficial face of the nail together with the fabric tape, and the correction tool EQ3 is secured to the nail while the curved state of the pincer nail is corrected (see FIGS. 11C to 11E). By using a fabric tape onto which an adhesive is applied, a pincer nail can be readily corrected even at home.

In the case of the present embodiment, the correction tool EQ3 may be provided as a correction tool EQ3' or a correction tool EQ3" in modified examples shown in FIGS. 14A and 14B. In these correction tools EQ3' and EQ3", a thick disc-like operating portion 46 is formed at a tip end of a substantially T-shaped abutting portion 45. The proximal end side of the abutting portion 45 is formed to be wide in the surface direction (lateral direction), and the proximal end side is partly notched. The engaging portion 47 is formed by being cut in advance into a trapezoidal shape so that it engages the right lateral end of the nail tip in the correction tool EQ3' while it engages the left lateral end in the correction tool EQ3".

Figure 15A:
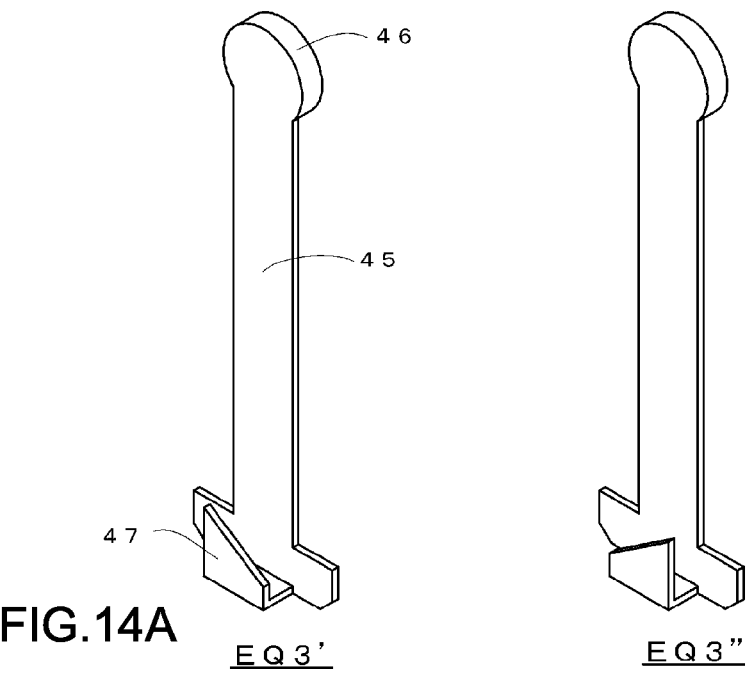
FIGS. 15A-15B include views each showing a correction tool EQ4 according to a fourth embodiment of the present invention.
Figure 15B:
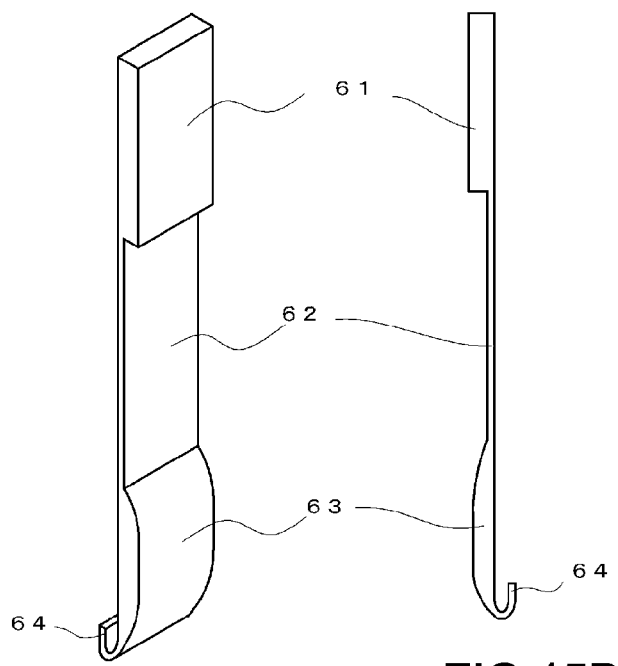

Next, FIGS. 15A-15B includes views of a pincer nail correction tool EQ4 according to a fourth embodiment of the present invention, namely a perspective view FIG. 15A and a right lateral view FIG. 15B.

The correction tool EQ4 is used for correction of moderate to severe ingrown nails, and is integrally formed by a flat operating portion 61, a thin-sheet connecting portion 62 extending from a back face side of a bottom face of the operating portion 61, an abutting portion 63 extending from a lower side tip end of the connecting portion and formed to have increasing thickness toward the front face, and a hook-like engaging portion 64 folded from a lower side tip end of the abutting portion 63. Then, the correction tool EQ4 is formed to have a vertical length of about 24 mm, for example.

The operating portion 61, the connecting portion 62 and the abutting portion 63 are formed to be flush with one another on their back faces. The front face side of the abutting portion 63 is formed to have increasing thickness in the shape of a trapezoid in lateral view.

Figure 16A:
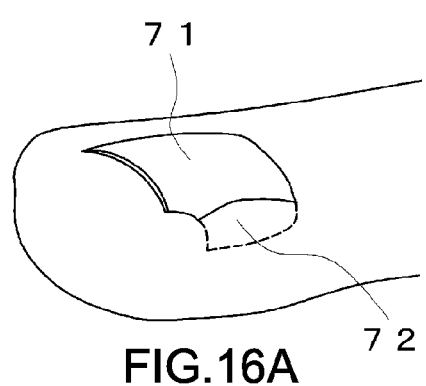
FIGS. 16A-16E include views each showing a method of using the correction tool EQ4.

Next, with use of FIGS. 16A-16E, a method of using the correction tool EQ4 configured as described above will be described. Here, the term "ingrown nail" refers to a condition that a lateral end of a nail 71 breaks into skin 72 as shown in FIG. 16A. The broken line part represents the part of the nail 71 situated inside the skin 72.

First, a sanitary treatment is conducted similarly to the first embodiment. Next, the mixture of the gel and the activator is applied onto the lower side of the inner face of the abutting portion 63 and onto the inner side of the engaging portion 64. At this time, the upper side of the abutting portion 63 is kept from being rubbed with the gel.

Figure 16B:
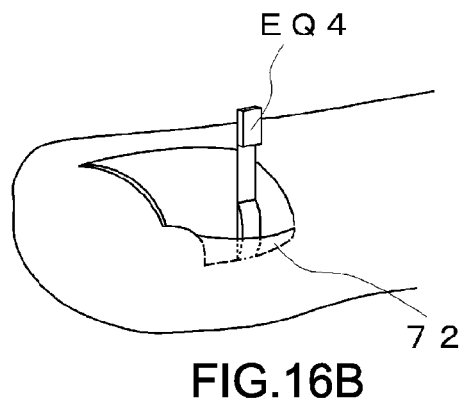
Figure 16C:
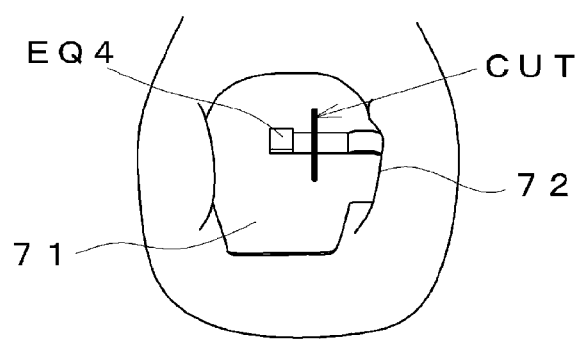

Next, as shown in FIG. 16B, a lateral nail fold of the subject is opened so that the lateral end of the nail 71 is visible, and the engaging portion 64 is hooked on the lateral end of the nail 71 and fixed. Thereafter, as the gel cures to secure the right lateral end of the nail 71 and the lower side of the correction tool EQ4, the gel is further poured between the superficial face of the nail 71 and the abutting portion 63 as well as the connecting portion 62. Next, as shown in FIG. 16C, the operating portion 61 is gripped and the correction tool EQ4 is brought down while the lateral end of the nail 71 is drawn up, whereby the superficial face of the nail 71, the upper side of the abutting portion 63, and the connecting portion 62 are joined together. The state that the correction tool EQ4 is brought down is kept until the gel cures, and the correction tool EQ4 and the nail 71 of the subject are integrated with each other while the curved state of the ingrown nail is corrected. The skin 72 is pushed to extend by the trapezoidal abutting portion 63.

Figure 16D:
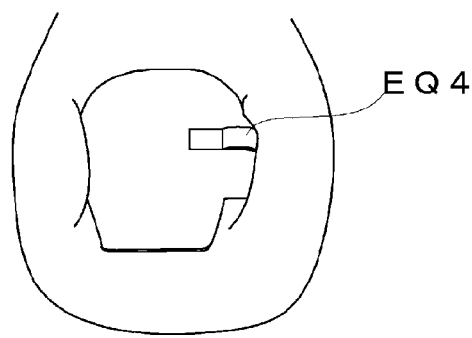
Figure 16E:
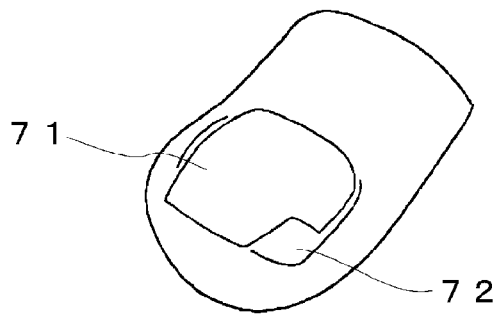

A part of the connecting portion 62 is cut along a cut line, a fiber glass is pasted on the superficial face of the nail 71, and the gel is applied thereon to complete the correction treatment of the ingrown nail (see FIG. 16D). Thereafter, according to the degree of remedy, for example, the correction tool EQ1 of the first embodiment is inserted into the nail 71 to correct the nail 71, and thus the ingrown state of the nail 71 is corrected as shown in FIG. 16E.

In the correction tool EQ4 of the fourth embodiment, since the abutting portion 63 is formed to be thick in the shape of a trapezoid, the skin 72 can be pushed to extend, and the nail 71 can be corrected while preventing the growing nail 71 from entering the skin 72.

Figure 17:
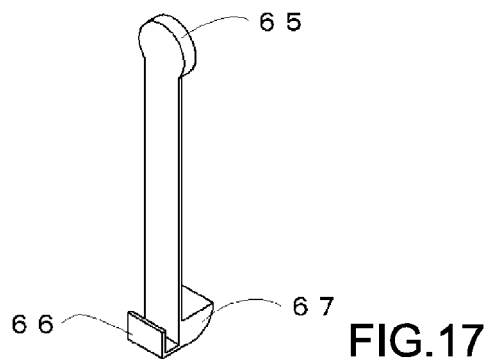
FIG. 17 is a view showing a correction tool EQ4' as another example of the correction tool EQ4.
Figures 18A, 18B:
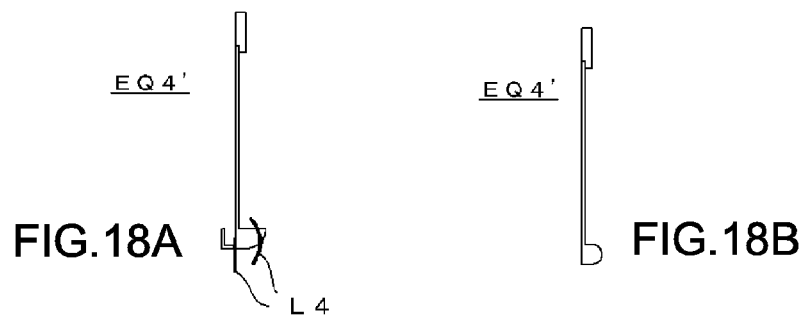
FIGS. 18A-18D include views each showing an example of using the correction tool EQ4'.
Figure 18C:
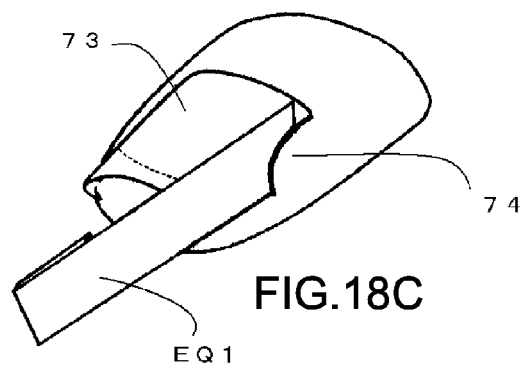
Figure 18D:
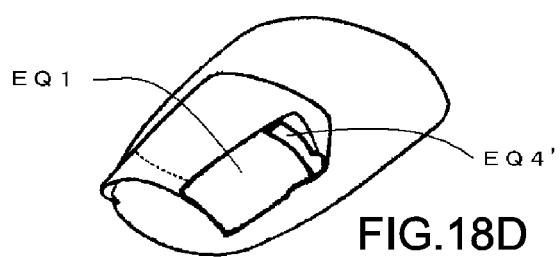

In the case of the present embodiment, the correction tool EQ4 may be provided as a correction tool EQ4' in a modified example shown in FIG. 17. In the correction tool EQ4', the operating portion 65 is formed into a thick disc-like shape. Further, an abutting portion 67 in the shape of an arc in front view is formed to project in the direction opposite to the hook-like engaging portion 66.

This correction tool EQ4' is also used similarly to the correction tool EQ4, and it may be used together with another correction tool. For example, as shown in FIGS. 18A-18D, by using the correction tool EQ1 of the first embodiment together with the correction tool EQ4', it is possible to efficiently correct the nail. First, the correction tool EQ4' is cut along a cut line L4 in advance (see FIGS. 18A and 18B). Then, into the nail in a condition that a lateral end of a nail 73 breaks into skin 74, the correction tool EQ1 is inserted (see FIG. 18C). Then, the operating portion 1 is rotated to fix the correction tool EQ1 to the nail, and an unnecessary part is cut off. After securing the correction tool EQ1, the skin 74 of the lateral end of the nail is opened, and the correction tool EQ4' is fixed onto the surface of the correction tool EQ1 so that the skin 74 is pushed to extend by the abutting portion 67 (see FIG. 18D). With this method, not only the lateral end of the nail breaking into the skin but also the tip end of the nail can be corrected at one time.

Figure 19:
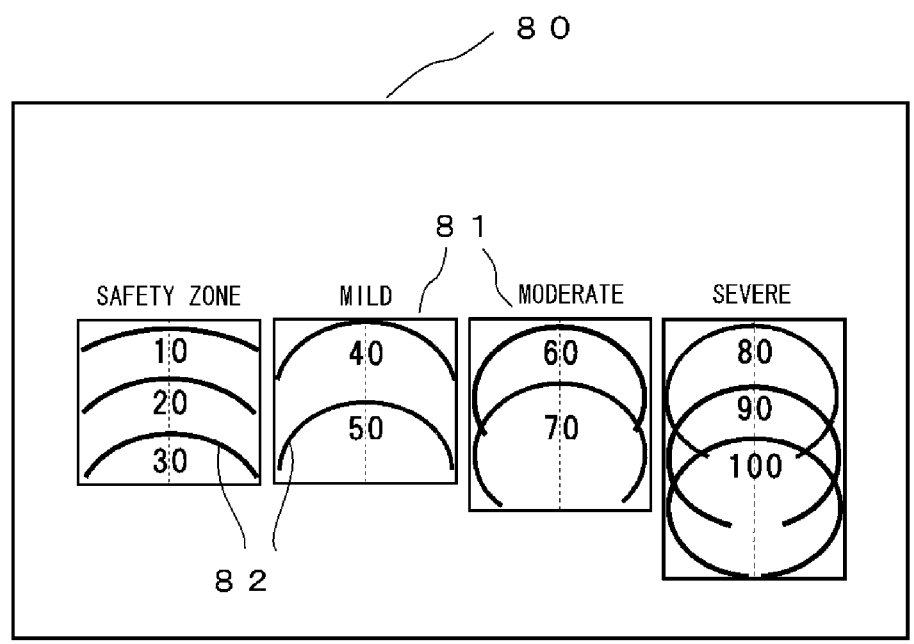
FIG. 19 is a view showing a pincer nail degree chart for determining a correction tool to be used.

Lastly, as for the correction tools EQ1-EQ4 of the present invention, a correction tool to be used may be changed appropriately depending on the degree of curvature of the pincer nail. For determining which one of the correction tools EQ1 to EQ4 is to be used, a pincer nail degree chart 80 as shown in FIG. 19 is used. The pincer nail degree chart 80 is a transparent sheet member in the size of a name card, on which a plurality of measuring portions 81 classified into "safety zone", "mild", "moderate" and "severe" depending on the severity of the degree of curvature of the nail are printed. These measuring portions have a plurality of arcs 82 formed to correspond to predetermined degrees of curvature of the nail.

This pincer nail degree chart 80 is placed in front of a toe, and the nail is compared with the arcs 82, and one of the arcs 82 corresponding to the degree of curvature of the nail is selected. By referring the classification to which the selected arc 82 belongs, one of the correction tools EQ1-EQ4 to be used is determined. For example, the correction tool EQ1 is used for 40 to 70 degrees, the correction tool EQ2 is used for 80 to 100 degrees, the correction tool EQ3 is used for 10 to 50 degrees or mild ingrown nails, and the correction tool EQ4 is used for moderate to severe ingrown nails.

The invention claimed is:

1. A pincer nail correction tool for remedying a pincer nail of a toe as the nail grows by integrally bonding a necessary part of the correction tool, which is separated from an operating flat plate of the correction tool, to the pincer nail, the tool comprising:

the operating flat plate having a first surface, an opposite second surface and end faces, to be gripped before the necessary part is bonded to the pincer nail and rotated in a direction in which the pincer nail is remedied;

a thin-sheet abutting portion having an outer surface to be exposed to a user and projecting straight toward a distal end, the outer surface extending from the first surface of the operating flat plate;

a thin-sheet engaging portion having a contact surface to be touched to the skin of the user and projecting straight toward the distal end, the contact surface shorter and narrower than a projecting length and width of the abutting portion extending from the second surface of the operating flat plate; and a bottom portion extending from one end face of the operating flat plate toward the distal end and connecting the abutting portion to the engaging portion, whereby the abutting portion, the engaging portion, and the bottom portion form a J-shaped cross-section, wherein the engaging portion includes a base part extending from the operating flat plate in a direction toward the distal end and a tip part extending from the base part toward the distal end, wherein the tip part being narrower than a width of the base part, and wherein the necessary part of the correction tool, which is bonded to the pincer nail and is separated from an operating flat plate, is formed of the abutting portion, the engaging portion, and the bottom portion.

2. The pincer nail correction tool according to claim 1, wherein the abutting portion is formed to be substantially rectangular.

3. The pincer nail correction tool according to claim 1, wherein the tip part is formed to be gradually narrower toward the distal end of the engaging portion.

4. The pincer nail correction tool according to claim 1, wherein the base part and the tip part are connected via an intermediate part formed to be gradually narrower toward the distal end of the engaging portion.

5. The pincer nail correction tool according to claim 1, wherein the abutting portion has a main part continuing from the operating flat plate, and a distal part thinner than the main part.

6. The pincer nail correction tool according to claim 1, wherein the bottom portion is notched at the distal end.

7. The pincer nail correction tool according to claim 6, wherein the abutting portion is provided with a plurality of holes.

8. A pincer nail remedying method using the tool according to claim 1, the method comprising:

putting the contact surface of the abutting portion in touch with the skin under the pincer nail;

rotating the operating flat plate together with the abutting portion, the engaging portion, and the bottom portion, so as to bond an inner surface of the abutting portion to an outer surface of the pincer nail;

waiting for the two said inner surface of the abutting portion and said outer surface of the pincer nail surfaces to be fixed by bonding; and making the necessary part by separating the abutting portion, the engaging portion, and the bottom portion, from the operating flat plate.

9. A pincer nail correction tool for remedying a pincer nail of a toe as the nail grows by integrally bonding a necessary part of the correction tool, which has been separated from an operating thick disc of the correction tool, to the pincer nail, the tool comprising:

the operating thick disc having a first surface and an opposite second surface;

an abutting portion, formed as a straight member, having one connected to a return portion and an opposite toward connected to the thick disc, so as to be handled in a cross direction of the pincer nail in order to touch an inner surface of the abutting portion to an outer surface of the nail, the inner surface of the abutting portion continuing to the first surface of the thick disc;

an engaging portion extending substantially to the abutting portion and projecting shorter than the abutting portion, said engaging portion and having a direct contact surface capable of being used to directly touch an inner surface of the pincer nail before the necessary part is bonded; and the return portion connecting the abutting portion with the engaging portion, whereby the abutting portion, the engaging portion, and the return portion form a J-shaped cross-section, wherein the abutting portion has a proximal end forming a substantially T-shape in planar view as a whole of the abutting portion, and wherein the necessary part, which is bonded to the pincer nail and is separated from the operating thick disc, includes said abutting portion, the engaging portion, and the return portion.

10. The pincer nail correction tool according to claim 9, wherein the engaging portion has a trapezoidal shape.

* * * * *